(12) United States Patent
Iguchi et al.

(10) Patent No.: US 10,557,790 B2
(45) Date of Patent: *Feb. 11, 2020

(54) CARBON ISOTOPE ANALYSIS DEVICE AND CARBON ISOTOPE ANALYSIS METHOD (71) Applicants: SEKISUI MEDICAL CO., LTD., Tokyo (JP); National University Corporation Nagoya University, Nagoya-shi, Aichi (JP)

(72) Inventors: Tetsuo Iguchi, Nagoya (JP); Hideki Tomita, Nagoya (JP); Norihiko Nishizawa, Nagoya (JP); Toshinari Oh-Hara, Tokyo (JP); Akira Ideno, Tokyo (JP)

(73) Assignees: SEKISUI MEDICAL CO., LTD., Tokyo (JP); NATIONAL UNIVERSITY CORPORATION NAGOYA UNIVERSITY, Nagoya-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/991,915

(22) Filed: May 29, 2018

(65) Prior Publication Data

US 2018/0275050 A1 Sep. 27, 2018

Related U.S. Application Data

(63) Continuation of application No. 15/234,554, filed on Aug. 11, 2016, now Pat. No. 10,012,586, which is a (Continued)

(30) Foreign Application Priority Data

Feb. 12, 2014 (JP) .................................. 2014-024890

(51) Int. Cl.
*G01N 21/3504* (2014.01)
*G02F 1/35* (2006.01)
(Continued)

(52) U.S. Cl.
CPC ......... *G01N 21/3504* (2013.01); *G01N 21/39* (2013.01); *G02B 17/004* (2013.01);
(Continued)

(58) Field of Classification Search
CPC .. G01N 21/3504; G01N 21/39; G01N 21/031; G01N 2201/06113;
(Continued)

(56) References Cited

U.S. PATENT DOCUMENTS 5,012,052 A * 4/1991 Hayes ................ G01N 30/7206
250/282
5,286,468 A * 2/1994 Chang .................... B01D 3/322
423/249

(Continued)

FOREIGN PATENT DOCUMENTS

JP 3390755 B2 3/2003
JP 2006-138752 A 6/2006
(Continued)

OTHER PUBLICATIONS

English translation of International Preliminary Report on Patentability dated Mar. 4, 2016, in PCT International Application No. PCT/JP2015/053875.
(Continued)

*Primary Examiner* — Taeho Jo
(74) *Attorney, Agent, or Firm* — Birch, Stewart, Kolasch & Birch, LLP (57) ABSTRACT

A method and apparatus for analyzing carbon isotope $^{14}C$ is provided. A carbon isotope analyzer including an isotopic carbon dioxide generator to generate isotopic carbon dioxide
(Continued)

from a carbon isotope; a spectrometer including an optical resonator having a pair of mirrors, and a photodetector to determine the intensity of light transmitted from the optical resonator; and a light generator including a light source, a first optical fiber to transmit a light beam from the light source, a second optical fiber for wavelength conversion, the second optical fiber branching from the first optical fiber at a point and combining with the first optical fiber at another point downstream of the branching point, and a non-linear optical crystal to generate light having the absorption wavelength of the isotopic carbon dioxide on the basis of the difference in frequency between light beams transmitted through the optical crystal.

15 Claims, 8 Drawing Sheets

Related U.S. Application Data continuation-in-part of application No. PCT/JP2015/053875, filed on Feb. 12, 2015.

(51) Int. Cl.

| | | |
|---|---|---|
| G02B 17/00 | (2006.01) | |
| G02F 1/355 | (2006.01) | |
| G02F 1/365 | (2006.01) | |
| G01N 21/03 | (2006.01) | |
| G01N 21/39 | (2006.01) | |

(52) U.S. Cl.
CPC .......... *G02F 1/3532* (2013.01); *G02F 1/3534* (2013.01); *G02F 1/3551* (2013.01); *G02F 1/365* (2013.01); *G01N 21/031* (2013.01); *G01N 2201/06113* (2013.01); *G01N 2201/08* (2013.01); *G02F 2201/02* (2013.01); *G02F 2203/56* (2013.01)

(58) Field of Classification Search
CPC  G01N 2201/08; G02B 17/004; G02F 1/3532; G02F 1/3534; G02F 1/3551; G02F 1/365; G02F 2201/02; G02F 2203/56
USPC ...................................................... 250/338.1
See application file for complete search history.

(56) References Cited

U.S. PATENT DOCUMENTS

| | | | | |
|---|---|---|---|---|
| 5,783,741 A * | 7/1998 | Ellis | ..................... | H01J 49/0422 250/288 |
| 5,818,580 A * | 10/1998 | Murnick | .............. | G01N 21/171 356/311 |
| 5,864,398 A * | 1/1999 | Murnick | ................. | G01N 21/62 356/311 |
| 5,929,442 A * | 7/1999 | Higashi | ................... | G01N 21/39 250/339.13 |
| 6,486,474 B1 * | 11/2002 | Owen | .................... | G01N 21/031 250/339.02 |
| 6,618,531 B1 | 9/2003 | Goto et al. | | |
| 6,800,855 B1 * | 10/2004 | Dong | ...................... | G01N 21/39 250/339.13 |
| 6,940,083 B2 * | 9/2005 | Mori | ..................... | A61B 5/0836 250/573 |
| 7,101,340 B1 * | 9/2006 | Braun | ..................... | A61B 5/097 128/920 |
| RE40,184 E * | 3/2008 | Lin | ......................... | A61F 9/008 372/37 |
| 8,539,816 B2 * | 9/2013 | Kachanov | .......... | G01N 21/1702 73/24.02 |
| 9,541,497 B2 * | 1/2017 | Heyne | .................. | A61B 5/0836 |
| 2002/0134940 A1 * | 9/2002 | Ohkubo | ............. | G01N 21/3504 250/339.13 |
| 2003/0146760 A1 * | 8/2003 | Kogawa | .................. | G01T 1/178 324/464 |
| 2003/0178589 A1 * | 9/2003 | Mori | .................... | A61B 5/0836 250/573 |
| 2003/0228708 A1 * | 12/2003 | Huber | ...................... | G01N 1/34 436/181 |
| 2006/0013270 A1 * | 1/2006 | Yunnoto | ................ | G01N 21/39 372/21 |
| 2007/0018091 A1 * | 1/2007 | Garner | ................... | B01D 59/44 250/283 |
| 2007/0074541 A1 * | 4/2007 | Badding | ............... | C03B 19/106 65/413 |
| 2007/0077167 A1 * | 4/2007 | Mori | ................... | G01N 21/3504 422/54 |
| 2007/0242720 A1 * | 10/2007 | Eckles | ................. | G01N 21/031 372/107 |
| 2008/0129994 A1 * | 6/2008 | Murnick | ............ | G01N 21/1717 356/318 |
| 2009/0233371 A1 | 9/2009 | Tashiro | | |
| 2010/0002234 A1 * | 1/2010 | Cormier | ............ | G01N 21/3504 356/436 |
| 2011/0155272 A1 * | 6/2011 | Conway | ............. | G01N 33/1846 137/896 |
| 2011/0242659 A1 * | 10/2011 | Eckles | ................. | G01N 21/031 359/508 |
| 2011/0270113 A1 * | 11/2011 | Heyne | .................. | A61B 5/0836 600/531 |
| 2011/0292377 A1 * | 12/2011 | Osenberg | ............... | G01D 5/268 356/73 |
| 2011/0302992 A1 * | 12/2011 | Robbins | ................. | A61B 5/083 73/23.3 |
| 2012/0133931 A1 * | 5/2012 | Ferman | ..................... | G01J 3/10 356/300 |
| 2012/0188550 A1 * | 7/2012 | Matsuda | ............ | G01N 21/3504 356/437 |
| 2012/0241622 A1 * | 9/2012 | Heyne | .................. | G01N 21/031 250/339.13 |
| 2012/0287418 A1 * | 11/2012 | Scherer | .................. | G01N 21/61 356/51 |
| 2012/0298868 A1 * | 11/2012 | Massick | ............ | G01N 21/3504 250/339.13 |
| 2013/0202006 A1 * | 8/2013 | Rudolph | ............. | H01S 3/06741 372/55 |
| 2013/0228688 A1 * | 9/2013 | Plusquellic | ............. | G01J 3/108 250/339.06 |
| 2013/0256939 A1 * | 10/2013 | Devenney | ............... | C04B 7/345 264/115 |
| 2013/0267035 A1 * | 10/2013 | Russo | .................... | G01N 21/75 436/171 |
| 2014/0114206 A1 * | 4/2014 | Joseph | ................ | G01N 33/0055 600/532 |
| 2014/0172323 A1 * | 6/2014 | Marino | ............. | G01N 21/3504 702/24 |
| 2014/0264031 A1 * | 9/2014 | Fermann | ................ | G01J 3/42 250/339.02 |
| 2014/0301938 A1 * | 10/2014 | Jeong | ..................... | B01D 59/34 423/461 |
| 2015/0355086 A1 * | 12/2015 | Gagliardi | .................. | G01J 3/02 356/326 |
| 2016/0054180 A1 * | 2/2016 | Giusfredi | .................. | G01J 3/42 250/339.07 |
| 2016/0069797 A1 * | 3/2016 | Chanda | .................. | G01N 21/39 356/437 |
| 2016/0084757 A1 * | 3/2016 | Miron | ..................... | G01N 21/39 356/437 |
| 2017/0059740 A1 * | 3/2017 | Perkins | ..................... | G01N 9/00 |
| 2017/0074779 A1 * | 3/2017 | Chanda | .................. | G01N 21/39 |

FOREIGN PATENT DOCUMENTS

| | | |
|---|---|---|
| JP | 2007-85874 A | 4/2007 |
| JP | 2007-212212 A | 8/2007 |
| JP | 2013-11620 A | 1/2013 |
| JP | 2013-515950 A | 5/2013 |

(56) References Cited

FOREIGN PATENT DOCUMENTS

| WO | WO 2011/157284 A | 12/2011 |
| WO | WO 2012/087710 A1 | 6/2012 |
| WO | WO 2013/078215 A1 | 5/2013 |

OTHER PUBLICATIONS

English translation of International Search Report dated Apr. 14, 2016, in PCT International Application No. PCT/JP2015/053875.
Extended European Search Report for European Application No. 15749373.5, dated Sep. 11, 2017.
Galli et al., "Molecular Gas Sensing Below Parts Per Trillion: Radiocarbon-Dioxide Optical Detection," Phys. Rev. Lett. (Dec. 30, 2011), No. 107, 270802-1-270802-4.
Galli et al., "Spectroscopic detection of radiocarbon dixoide at parts-per-quadrillion sensitivity," Optica (Apr. 2006), vol. 3, No. 4, pp. 385-388.
Galli et al., "Ti:sapphire Laser Intracavity Difference-Frequency Generation of 30mW cw Radiation Around 4.5 μm," Optics Letters, Optical Society of America, vol. 35, No. 21, Nov. 1, 2010 (published Oct. 21, 2010), pp. 3616-3618.
Hiromoto et al., "Cavity Ring-down Bunko ni Motozuku 14C Renzoku Monitoring no Sekkei Kento," Atomic Energy Society of Japan Haru no Nenkai Yokoshu, Mar. 19, 2010, p. 432.
Galli et al., "Optical Detection of Radiocarbon Dioxide: First Results and AMS Intercomparison," Radiocarbon, 2013, vol. 55, Nr 2-3, pp. 213-223.

\* cited by examiner

51: OPTICAL RESONATOR
52: HIGHLY REFLECTIVE MIRROR
53: RING PIEZOELECTRIC ACTUATOR
54: WATER-COOLING HEATSINK
55: MIRROR DRIVING MECHANISM
56: GAS CELL FOR ANALYSIS
58: ADIABATIC CHAMBER
59: PELTIER ELEMENT

FIG.7

FIG.8

CARBON ISOTOPE ANALYSIS DEVICE AND CARBON ISOTOPE ANALYSIS METHOD

CROSS-REFERENCE TO RELATED APPLICATIONS

This application is a Continuation of copending U.S. application Ser. No. 15/234,554, filed on Aug. 11, 2016 which is a Continuation-in-Part of PCT International Application No. PCT/JP2015/053875, filed on Feb. 12, 2015, which claims priority under 35 U.S.C. 119(a) to Patent Application No. 2014-024890, filed in Japan on Feb. 12, 2014, all of which are hereby expressly incorporated by reference into the present application. The present application also relates to Japanese patent application No. 2015-035912, filed in Japan on Feb. 25, 2015, the entire contents of which is hereby incorporated by reference into the present application.

TECHNICAL FIELD

The present invention relates to a carbon isotope analyzer and a method of analyzing carbon isotopes. In specific, the present invention relates to a radioactive carbon isotope analyzer useful for analysis of radioactive carbon $^{14}C$ and a method of analyzing the radioactive carbon isotope.

BACKGROUND ART

Carbon isotope analysis has been applied in a variety of fields, including assessment of environmental dynamics based on the carbon cycle, and historical and empirical research through radiocarbon dating. The natural abundances of carbon isotopes, which may vary with regional or environmental factors, are as follows: 98.89% for $^{12}C$ (stable isotope), 1.11% for $^{13}C$ (stable isotope), and 1× $10^{-10}$% for $^{14}C$ (radioisotope). These isotopes, which have different weights, exhibit the same chemical behavior. Thus, artificial enrichment of an isotope of low abundance and accurate analysis of the isotope can be applied to observation of a variety of reactions.

In the clinical field, in vivo administration and analysis of a compound labeled with, for example, radioactive carbon $^{14}C$ are very useful for assessment of drug disposition. For example, such a labeled compound is used for practical analysis in Phase I or Phase IIa. Administration of a compound labeled with radioactive carbon $^{14}C$ (hereinafter may be referred to simply as "$^{14}C$") to a human body at a very small dose (hereinafter may be referred to as "microdose") (i.e., less than the pharmacologically active dose of the compound) and analysis of the labeled compound are expected to significantly reduce the lead time for a drug discovery process because the analysis provides findings on drug efficacy and toxicity caused by drug disposition.

Examples of the traditional $^{14}C$ analysis include liquid scintillation counting (hereinafter may be referred to as "LSC") and accelerator mass spectrometry (hereinafter may be referred to as "AMS").

LSC involves the use of a relatively small table-top analyzer and thus enables convenient and rapid analysis. Unfortunately, LSC cannot be used in clinical trials because of its high $^{14}C$ detection limit (10 dpm/mL). In contrast, AMS can be used in clinical trials because of its low $^{14}C$ detection limit (0.001 dpm/mL), which is less than one thousandth of that of LSC. Unfortunately, the use of AMS is restricted because AMS requires a large and expensive analyzer. Since only several tens of AMS analyzers are provided in Japan, analysis of one sample requires about one week due to a long waiting time for samples to be analyzed. Thus, a demand has arisen for development of a convenient and rapid method of analyzing $^{14}C$.

RELATED ART

Patent Document 1: Japanese Patent No. 3390755

Non-Patent Document

Non-Patent Document 1: I. Galli, et al., Phy. Rev. Lett. 2011, 107, 270802

SUMMARY OF INVENTION

Several techniques have been proposed for solving the aforementioned problems (see Non-Patent Document 1 and Patent Document 1, for example).

Since I. Galli, et al. demonstrated the analysis of $^{14}C$ of natural abundance level by cavity ring-down spectroscopy (hereinafter may be referred to as "CRDS") in Non-Patent Document 1, this analysis has received attention.

Although the $^{14}C$ analysis by CRDS has been demonstrated, this analysis involves the use of a 4.5 µm laser beam generator having a very intricate structure. Thus, a demand has arisen for a simple and convenient apparatus or method for analyzing $^{14}C$.

Patent Document 1 discloses a wavelength-tunable short optical pulse generator that can readily generate short optical pulses. Unfortunately, this generator cannot generate a 4.5 µm laser beam and thus cannot be used for $^{14}C$ analysis.

In view of the foregoing, an object of the present invention is to provide a simple and convenient apparatus capable of analyzing isotopic carbon $^{14}C$ and a method of analyzing the carbon isotope.

Solution to Problem

The present invention provides:

Aspect <1> A carbon isotope analyzer including an isotopic carbon dioxide generator to generate isotopic carbon dioxide from a carbon isotope; a spectrometer including an optical resonator having a pair of mirrors, and a photodetector to determine the intensity of light transmitted from the optical resonator; and a light generator including a light source, a first optical fiber to transmit a light beam from the light source, a second optical fiber for wavelength conversion, the second optical fiber branching from the first optical fiber at a point and combining with the first optical fiber at another point downstream of the branching point, and a non-linear optical crystal to generate light having the absorption wavelength of the isotopic carbon dioxide on the basis of the difference in frequency between light beams transmitted through the optical crystal.

Aspect <2> The carbon isotope analyzer according to Aspect <1>, wherein the carbon isotope is radioactive carbon $^{14}C$, and the isotopic carbon dioxide is radioactive carbon dioxide $^{14}CO_2$.

Aspect <3> The carbon isotope analyzer according to Aspect <1> or <2>, wherein the light source generates an optical frequency comb.

Aspect <4> The carbon isotope analyzer according to any one of Aspects <1> to <3>, wherein the light source is a fiber laser source.

Aspect <5> The carbon isotope analyzer according to any one of Aspects <1> to <4>, wherein the light having the absorption wavelength of the isotopic carbon dioxide is light of 4.5 μm region.

Aspect <6> The carbon isotope analyzer according to any one of Aspects <1> to <5>, wherein the isotopic carbon dioxide generator generates the isotopic carbon dioxide from the carbon isotope with a total organic carbon generator.

Aspect <7> The carbon isotope analyzer according to any one of Aspects <1> to <6>, wherein the first optical fiber extends from the light source to the optical resonator.

Aspect <8> The carbon isotope analyzer according to any one of Aspects <1> to <7>, wherein the first optical fiber includes a first optical fiber segment a extending between the light source and the non-linear optical crystal and a first optical fiber segment b for mid-infrared light extending between the non-linear optical crystal and the optical resonator.

Aspect <9> The carbon isotope analyzer according to any one of Aspects <1> to <6> and <8>, wherein the light generator further includes a light transmitter to transmit light from the non-linear optical crystal to the optical resonator.

Aspect <10> The carbon isotope analyzer according to Aspect <9>, wherein the first optical fiber is the first optical fiber segment a extending between the light source and the non-linear optical crystal.

Aspect <11> The carbon isotope analyzer according to any one of Aspects <1> to <6> and <8> to <10>, wherein the light generator further includes an optical lens between the non-linear optical crystal and the point at which the first optical fiber combines with the second optical fiber, and/or between the non-linear optical crystal and the optical resonator.

Aspect <12> The carbon isotope analyzer according to any one of Aspects <1> to <11>, wherein a downstream end of the first optical fiber is in contact with one of the mirrors.

Aspect <13> The carbon isotope analyzer according to any one of Aspects <1> to <12>, wherein the second optical fiber is composed of a non-linear fiber.

Aspect <14> The carbon isotope analyzer according to any one of Aspects <1> to <13>, wherein the spectrometer further includes a cooler to cool the optical resonator.

Aspect <15> The carbon isotope analyzer according to any one of Aspects <1> to <14>, wherein the spectrometer further includes a vacuum unit accommodating the optical resonator.

Aspect <16> The carbon isotope analyzer according to any one of Aspects <1> to <15>, wherein the spectrometer further includes a vibration absorber.

Aspect <17> The carbon isotope analyzer according to any one of Aspects <1> to <16>, wherein the spectrometer further includes a diffraction grating to disperse the transmitted light into spectral components of different wavelengths, and the photodetector includes a sub-photodetector a and a sub-photodetector b to detect the spectral components of different wavelengths.

Aspect <18> A method of analyzing a carbon isotope, including forming isotopic carbon dioxide from a carbon isotope; feeding the isotopic carbon dioxide into an optical resonator having a pair of mirrors; generating a plurality of light beams having different wavelengths from a light source, and transmitting the light beams through a non-linear optical crystal, to generate incident light on the basis of the difference in frequency between the light beams, the incident light having the absorption wavelength of the isotopic carbon dioxide; applying the incident light to the isotopic carbon dioxide, and determining the intensity of transmitted light generated through resonance of the incident light; and calculating the concentration of the carbon isotope on the basis of the intensity of the transmitted light.

Aspect <19> The method according to Aspect <18>, wherein the carbon isotope is radioactive carbon $^{14}C$, and the isotopic carbon dioxide is radioactive carbon dioxide $^{14}CO_2$.

Aspect <20> The method according to Aspect <18> or <19>, wherein the incident light is light of 4.5 μm region.

Aspect <21> The method according to any one of Aspects <18> to <20>, wherein an optical frequency comb is generated from the light source.

Aspect <22> The method according to any one of Aspects <18> to <21>, wherein the light source is a fiber laser source.

Aspect <23> The method according to any one of Aspects <18> to <22>, wherein the intensity of the transmitted light is determined while a downstream end of a first optical fiber is brought into contact with one of the mirrors to prevent the transmitted light from coming into contact with air.

Aspect <24> The method according to any one of Aspects <18> to <23>, wherein the intensity of the transmitted light is determined while the isotopic carbon dioxide is cooled to 273K (0° C.) or less.

Aspect <25> The method according to any one of Aspects <18> to <24>, wherein first light from the light source is transmitted through the first optical fiber; the first light is also transmitted through a second optical fiber for wavelength conversion, to generate second light having a wavelength different from that of the first light, the second optical fiber branching from the first optical fiber at a point; the second light is combined with the first light transmitted through the first optical fiber downstream of the point; and the first light and the second light are transmitted through the non-linear optical crystal, to generate incident light on the basis of the difference in frequency between the first light and the second light, the incident light having the absorption wavelength of the isotopic carbon dioxide.

Aspect <26> The method according to any one of Aspects <18> to <25>, wherein the first optical fiber extends from the light source to the optical resonator.

Aspect <27> The method according to any one of Aspects <18> to <26>, wherein the first optical fiber includes a first optical fiber segment a extending between the light source and the non-linear optical crystal and a first optical fiber segment b for mid-infrared light extending between the non-linear optical crystal and the optical resonator.

Aspect <28> The method according to any one of Aspects <18> to <27>, wherein the second optical fiber is composed of a non-linear fiber.

Aspect <29> The method according to any of Aspects <18> to <28>, wherein the isotopic carbon dioxide is cooled before being introduced into the spectrometer.

Aspect <30> The method according to any one of Aspects <18> to <29>, wherein the intensity of the transmitted light is determined while the optical resonator is maintained under vacuum.

Aspect <31> The method according to any one of Aspects <18> to <30>, wherein the intensity of the transmitted light is determined under absorption of external vibration to the optical resonator.

Aspect <32> The method according to any one of Aspects <18> to <31>, wherein the transmitted light is dispersed into different spectral components, and the intensities of the spectral components are determined.

Aspect <33> The carbon isotope analyzer according to claim 2, wherein detection sensitivity of the $^{14}C$ analyzer to the radioactive carbon isotope $^{14}C$ is 0.1 dpm/mL.

Effects of Invention

The present invention provides a simple and convenient apparatus capable of analyzing isotopic carbon $^{14}C$ and a method of analyzing the isotopic carbon.

DESCRIPTION OF EMBODIMENT

The present invention will now be described with reference to embodiments, which should not be construed to limit the invention. Components having identical or similar functions are denoted by identical or similar reference numerals without redundant description. In the schematic drawings, specific dimensions should be determined in consideration of the following description. Certainly, the drawings also include different relationships and ratios of dimensions.
(Carbon Isotope Analyzer)

Figure 1:
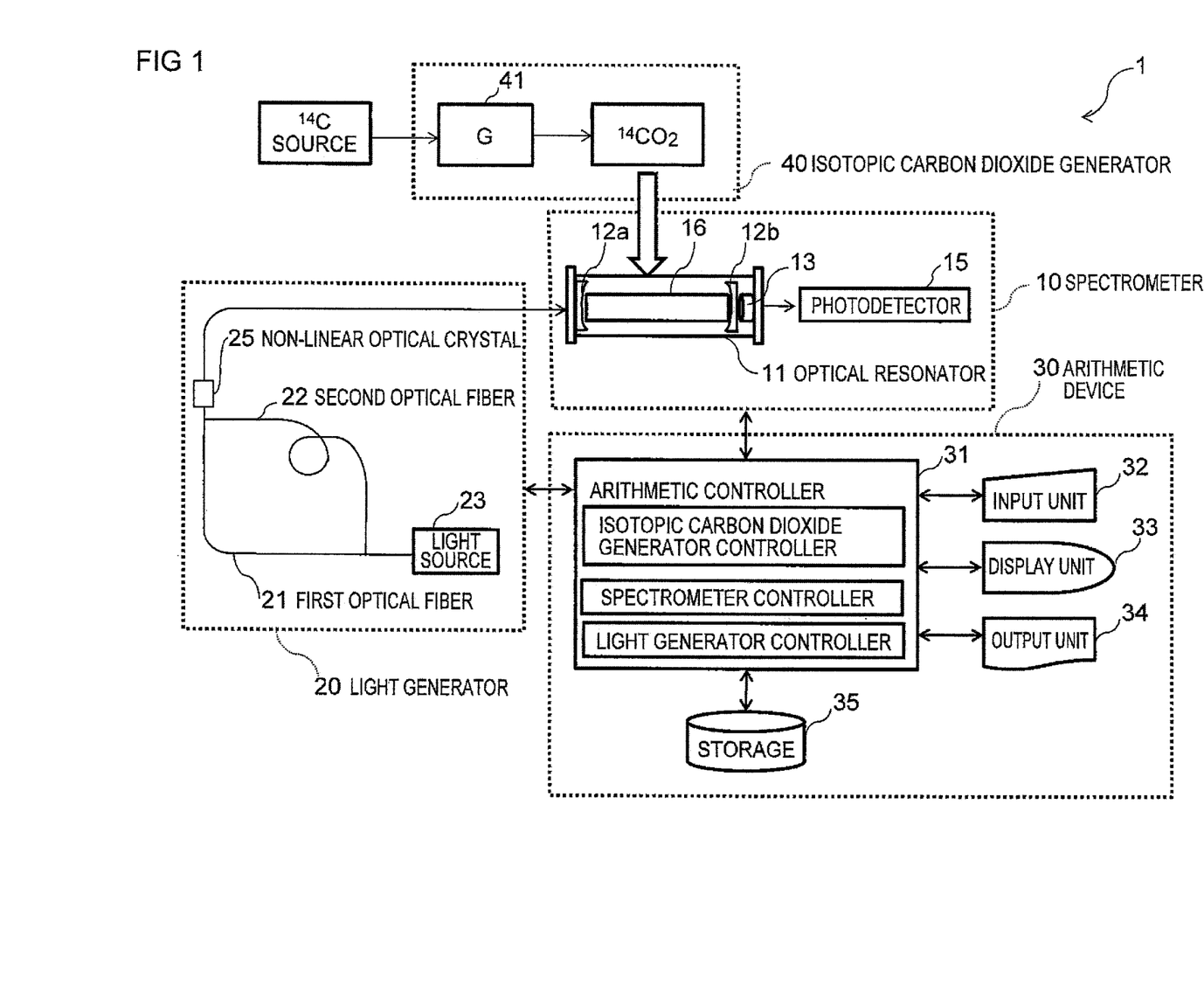
FIG. 1 is a schematic illustration of a carbon isotope analyzer.

FIG. 1 is a schematic illustration of a carbon isotope analyzer. The carbon isotope analyzer 1 includes an isotopic carbon dioxide generator 40, a light generator 20, a spectrometer 10, and an arithmetic device 30. In the following description, the analyte is radioactive carbon $^{14}C$. The isotopic carbon dioxide $^{14}CO_2$ generated from the radioisotope $^{14}C$ absorbs light of 4.5 µm region. As detailed below, high sensitivity can be achieved by appropriate combination of the absorption line of the analyte, a light generator, and an optical resonator mode.
<Spectrometer>

As illustrated in FIG. 1, the spectrometer 10 includes an optical resonator (or optical cavity) 11 and a photodetector 15 to determine the intensity of light transmitted from the optical resonator 11. The optical resonator 11 includes a cylindrical body to be filled with the target isotopic carbon dioxide; a pair of highly reflective mirrors 12a and 12b (reflectance: 99.99% or more) respectively disposed at first and second longitudinal ends of the body such that the concave faces of the mirrors confront each other; a piezoelectric element 13 disposed at the second end of the body to adjust the distance between the mirrors 12a and 12b; and a cell 16 to be filled with an analyte gas. Although not illustrated, the side of the body is preferably provided with a gas inlet through which the isotopic carbon dioxide is injected and a port for adjusting the pressure in the body.

A laser beam incident on the optical resonator 11 repeatedly reflects between the mirrors over several thousand to ten thousand times while the optical resonator 11 emits light at an intensity corresponding to the reflectance of the mirrors. Thus, the effective optical path length of the laser beam reaches several tens of kilometers, and a trace amount of analyte gas contained in the optical resonator absorbs a large fraction of the laser beam.

Figure 2A:
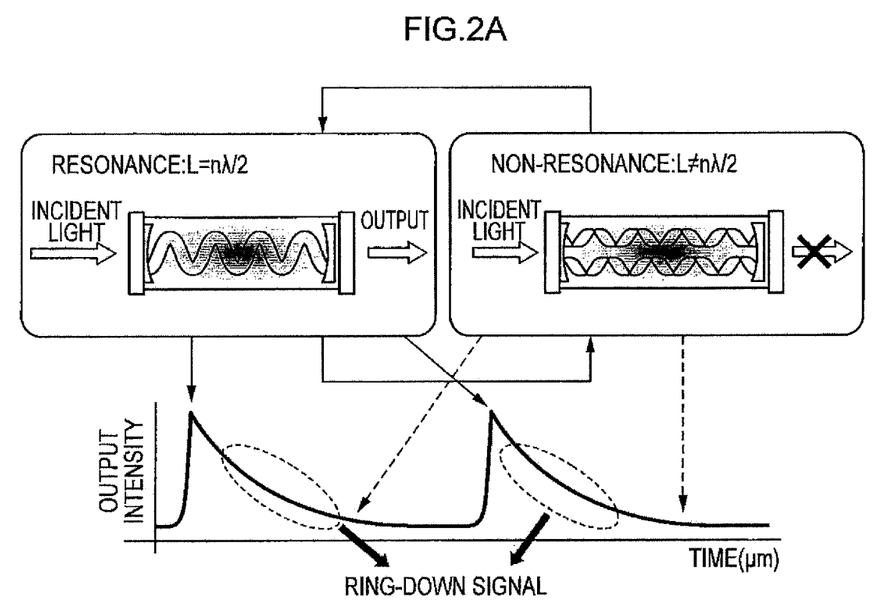
FIGS. 2A and 2B illustrate the principle of laser-based high-speed cavity ring-down spectroscopy.
Figure 2B:
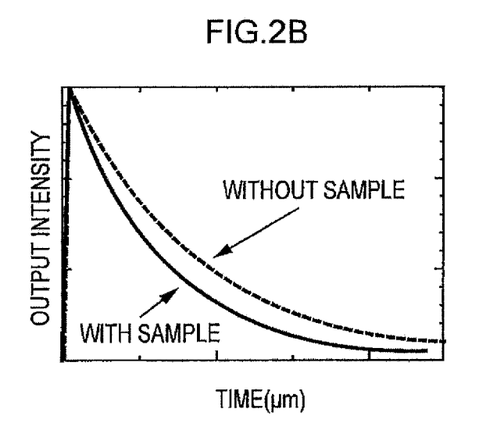

FIGS. 2A and 2B illustrate the principle of laser-based high-speed cavity ring-down spectroscopy (hereinafter may be referred to as "CRDS").

As illustrated in FIG. 2A, a signal of high intensity is output from the optical resonator in a resonance state between the mirrors. In contrast, no signal is detected due to optical interference in a non-resonance state caused by a change in distance between the mirrors through operation of the piezoelectric element 13. Thus, an exponential decay signal (ring-down signal) as shown in FIG. 2A is observed through a rapid change in length of the optical resonator (i.e., a rapid change from the resonance state to the non-resonance state). Such a ring-down signal may be observed by rapid shielding of the incident laser beam with an optical switch 26 (see FIG. 3).

The dotted curve in FIG. 2B corresponds to a time-dependent ring-down signal output from the optical resonator in the case of the absence of a light-absorbing substance in the optical resonator. In contrast, the solid curve in FIG. 2B corresponds to the case of the presence of a light-absorbing substance in the optical resonator. In this case, the light decay time is shortened because of absorption of the laser beam by the light-absorbing substance during repeated reflection of the laser beam in the optical resonator. The light decay time depends on the concentration of the light-absorbing substance in the optical resonator and the wavelength of the incident laser beam. Thus, the absolute concentration of the light-absorbing substance can be calculated on the basis of the Beer-Lambert law ii. The concentration of the light-absorbing substance in the optical resonator may be determined through measurement of a variation in ring-down rate, which is proportional to the concentration of the light-absorbing substance.

The light from the optical resonator is detected by the photodetector, and the concentration of $^{14}CO_2$ is calculated with the arithmetic device. The concentration of $^{14}C$ is then calculated from the concentration of $^{14}CO_2$.

Figure 5:
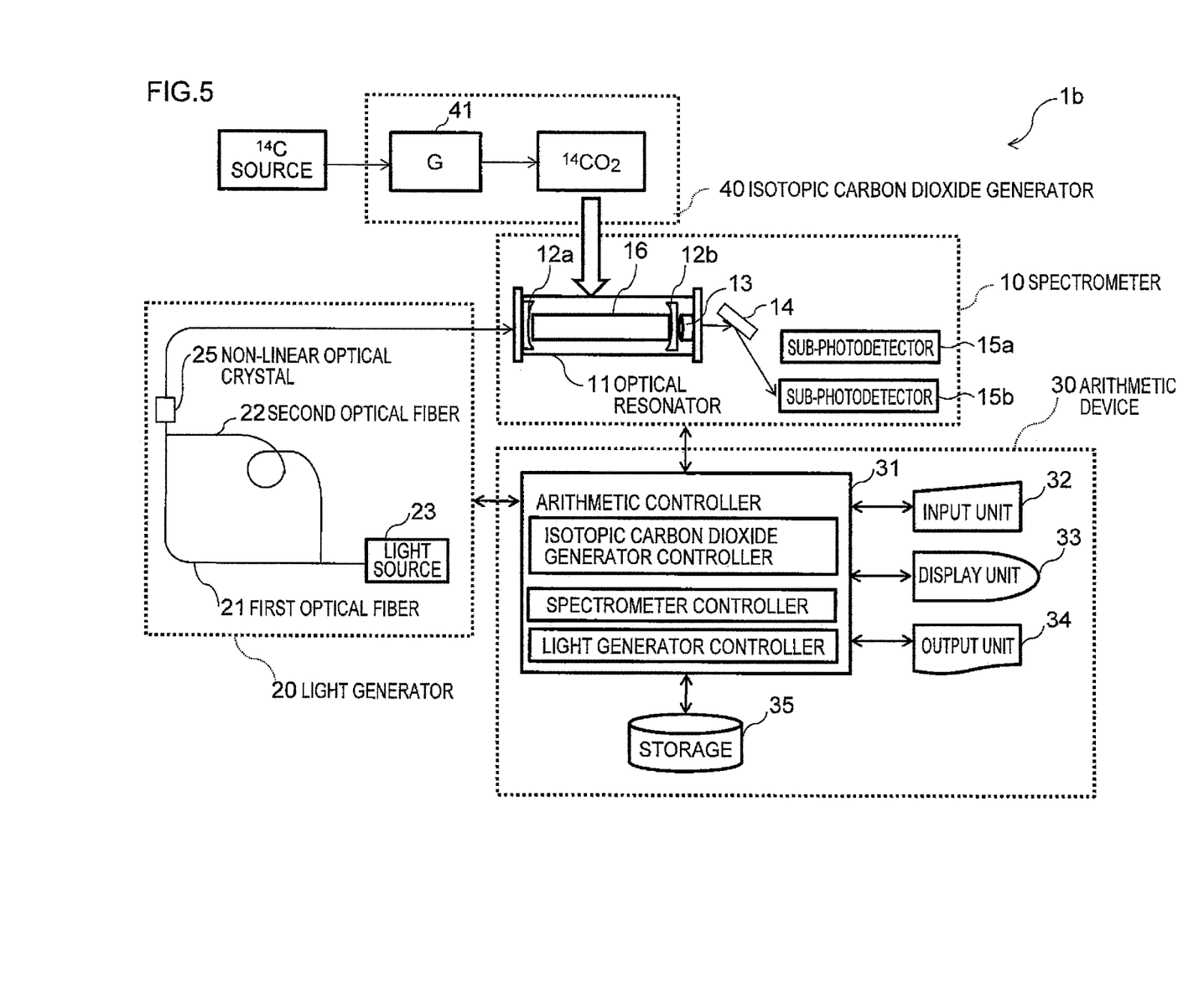
FIG. 5 is a schematic illustration of modification 2 of the carbon isotope analyzer.

The photodetector may be used in combination with a diffraction grating 14 to detect light having a specific wavelength (see FIG. 5). Details will be described below together with the light generator.

The distance between the mirrors 12a and 12b in the optical resonator 11, the curvature radius of the mirrors 12a and 12b, and the longitudinal length and width of the body are preferably varied depending on the absorption wavelength of the isotopic carbon dioxide (i.e., analyte). The length of the optical resonator is adjusted to 1 mm to 10 m, for example.

An increase in length of the optical resonator contributes to securement of an effective optical path length, but leads to an increase in volume of the gas cell, resulting in an increase in amount of a sample required for the analysis. Thus, the length of the optical resonator is preferably 10 cm to 60 cm in the case of isotopic carbon dioxide $^{14}CO_2$. Preferably, the curvature radius of the mirrors 12a and 12b is equal to or slightly longer than the length of the optical resonator.

The distance between the mirrors can be adjusted to, for example, several micrometers to several tens of micrometers through the driving of the piezoelectric element 13. The distance between the mirrors can be finely adjusted by the piezoelectric element 13 for preparation of an optimal resonance state. The aforementioned mirrors 12a and 12b (i.e., a pair of concave mirrors) may be replaced with combination of a concave mirror and a planar mirror or combination of two planar mirrors, so long as a sufficient optical path can be provided.

The mirrors 12a and 12b may be composed of sapphire glass.

The cell 16 to be filled with the analyte gas preferably has a small volume because even a small amount of the analyte effectively provides optical resonance. The volume of the cell 16 may be 8 mL to 1,000 mL. The cell volume can be appropriately determined depending on the amount of a $^{14}C$ source to be analyzed. For example, the cell volume is preferably 80 mL to 120 mL for a $^{14}C$ source that is available in a large amount (e.g., urine), and is preferably 8 mL to 12 mL for a $^{14}C$ source that is available only in a small amount (e.g., blood or teat fluid).

Evaluation of Stability Condition of Optical Resonator

The $^{14}CO_2$ absorption and detection limit of CRDS were calculated on the basis of spectroscopic data. Spectroscopic data on $^{12}CO_2$ and $^{13}CO_2$ were obtained from the high-resolution transmission molecular absorption database (HITRAN), and spectroscopic data on $^{14}CO_2$ were obtained from the reference "S. Dobos, et al., Z. Naturforsch, 44a, 633-639 (1989)."

A variation ($\Delta\beta$) in ring-down rate (exponential decay rate) caused by $^{14}CO_2$ absorption ($\Delta\beta=\beta-\beta_0$ where $\beta$ is a decay rate in the presence of a sample, and $\beta_0$ is a decay rate in the absence of a sample) is represented by the following expression:

$$\Delta\beta=\sigma_{14}(\lambda,T,P)N(T,P,X_{14})c$$

where $\sigma_{14}$ represents the photoabsorption cross section of $^{14}CO_2$, N represents the number density of molecules, c represents the speed of light, and $\sigma_{14}$ and N are the function of $\lambda$ (the wavelength of laser beam), T (temperature), P (pressure), and $X_{14}=^{14}C/^{Total}C$).

Figure 7:
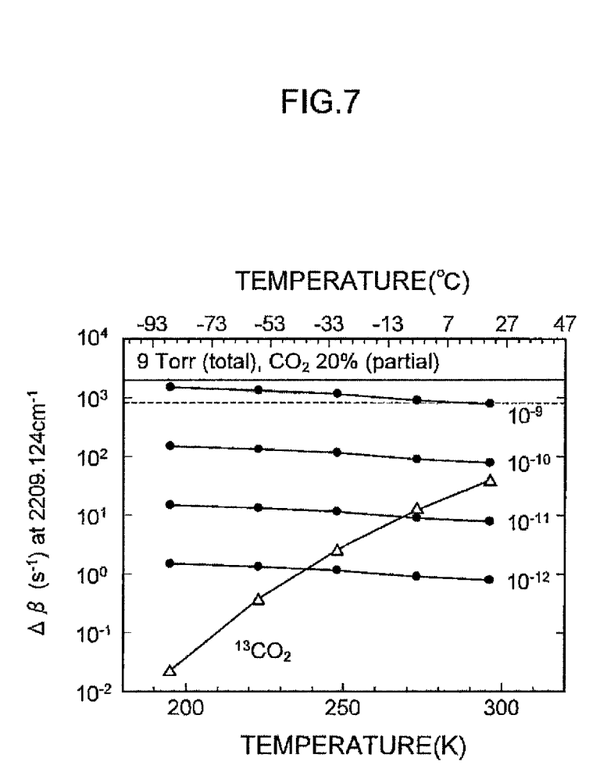
FIG. 7 illustrates the temperature dependence of a variation ($\Delta\beta$) upon $^{13}CO_2$ absorption or $^{14}CO_2$ absorption in CRDS.

FIG. 7 illustrates the calculated temperature dependence of $\Delta\beta$ upon $^{13}CO_2$ absorption or $^{14}CO_2$ absorption. As illustrated in FIG. 7, $^{13}CO_2$ absorption is equal to or higher than 14CO2 absorption at 300K (room temperature) in the case of a $^{14}C/^{Total}C$ of $10^{-10}$, $10^{-11}$, or $10^{-12}$, and the analysis requires cooling in such a case.

If a variation ($\Delta\beta_0$) in ring-down rate (corresponding to noise derived from the optical resonator) can be reduced to a level on the order of $10^1$ s$^{-1}$, the analysis can be performed at a $^{14}C/^{Total}C$ on the order of $10^{-11}$. Thus, cooling at about $-40°$ C. is required during the analysis.

The cooler used in the analysis and the cooling temperature will be detailed below in modification 1 of the carbon isotope analyzer.

<Light Generator>

The light generator 20 may be of any type that can generate light having the absorption wavelength of the isotopic carbon dioxide. Now will be described a compact light generator that can readily generates light of 4.5 μm, which is the absorption wavelength of isotopic carbon dioxide $^{14}CO_2$. The light generator 20 includes a light source 23, a first optical fiber 21 and a second optical fiber 22 to generate light beams having different frequencies from the light source 23, and a non-linear optical crystal 25 to generate light having the absorption wavelength of the isotopic carbon dioxide on the basis of the difference in frequency between the light beams transmitted through the optical crystal.

The light source 23 is preferably a short-wavelength pulse generator in view of generation of an optical comb-shaped spectrum with regular wavelength intervals (hereinafter may be referred to as "optical comb"). If the light source is a continuous wave generator, wavelength intervals increase at the center of the resultant optical spectrum; i.e., failure to generate an optical comb-shaped spectrum with regular wavelength intervals.

The light source 23 may be, for example, a solid-state laser, semiconductor laser, or fiber laser that generates short pulses by mode locking. Particularly preferred is a fiber laser, which is a compact and practical light source having high environmental stability.

The fiber laser may be an erbium (Er) fiber laser (1.55 μm beam) or an ytterbium (Yb) fiber laser (1.04 μm beam). An Er fiber laser is preferred from the economical viewpoint, whereas a Yb fiber laser is preferred in view of enhancement of optical absorption intensity.

The first optical fiber 21 transmits a light beam from the light source. The second optical fiber 22 for wavelength conversion branches from the first optical fiber 21 at a point and combines with the first optical fiber 21 at a point downstream of the branching point. The first optical fiber 21 may extend from the light source to the optical resonator.

The downstream end of the first optical fiber 21 is preferably in contact with the mirror 12a. In such a case, the light transmitted from the optical resonator 11 is prevented from coming into contact with air, resulting an increase in accuracy of measurement of the intensity of the transmitted light.

The first optical fiber 21 is preferably an optical fiber that can transmit high intensity of light of ultrashort pulses while maintaining the optical properties of the pulses. The first optical fiber 21 is preferably composed of fused quartz.

The second optical fiber 22 is preferably an optical fiber having anomalous dispersion and capable of efficient generation of long-wavelength ultrashort pulses by stimulated Raman scattering and the soliton effect. The second optical fiber 22 may be, for example, a polarization-maintaining fiber, a single-mode fiber, a photonic crystal fiber, or a photonic bandgap fiber. The optical fiber preferably has a length of several meters to several hundred meters depending on the wavelength shift. The second optical fiber 22 is preferably composed of fused quartz.

Difference frequency generation (hereinafter may be referred to as "DFG") can be used to generate difference-frequency light. In detail, the light beams of different frequencies (wavelengths) from the first and second optical fibers 21 and 22 transmit through the non-linear optical crystal, to generate difference-frequency light on the basis of the frequency difference. Thus, two light beams having wavelengths $\lambda_1$ and $\lambda_2$ generated from the light source 23 transmit through the non-linear optical crystal, to generate light of 4.5 μm (i.e., the absorption wavelength of the isotopic carbon dioxide) on the basis of the frequency difference. In the case of the use of the non-linear optical crystal, the DFG conversion efficiency depends on the photon density of light beams having different wavelengths ($\lambda_1, \lambda_2, \ldots \lambda_x$). Thus, difference-frequency light can be generated from a single pulse laser light source through DFG.

The resultant light of 4.5 μm region is an optical comb composed of a spectrum of frequencies (modes) with regular intervals ($f_r$) each corresponding to one pulse (frequency $f=f_{ceo}+N\cdot f_r$, N: mode number). CRDS using the optical comb requires extraction of light having the absorption wavelength of the analyte.

In the case of the carbon isotope analyzer disclosed in Non-Patent Document 1 by I. Galli, et al., laser beams having different wavelengths are generated from two laser devices, and light having the absorption wavelength of the isotopic carbon dioxide is generated on the basis of the difference in frequency between these laser beams. Thus, the analyzer has a large size and requires an intricate operation. The two beams generated from the two light sources exhibit different widths and timings of fluctuation, and the fluctuation of light composed of the two beams is difficult to reduce. Thus, the analyzer requires a device for controlling the fluctuation of light. In contrast, the light generator according to the embodiment of the present invention includes one fiber laser light source, optical fibers having a length of several meters, and a non-linear optical crystal. Thus, the light generator has a small size and is easy to carry and operate. Since two light beams are generated from a single light source, these beams exhibit the same width and timing of fluctuation, and thus the fluctuation of optical frequency can be readily cancelled through difference frequency generation without use of a fluctuation controller.

In some embodiments, a laser beam may be transmitted through air between the optical resonator and the joint of the first optical fiber with the second optical fiber. Alternatively, the optical path between the optical resonator and the combining point may optionally be provided with an optical transmission device including an optical system for convergence and/or divergence of a laser beam with a lens. In a more preferred embodiment, the optical path between the light source and the optical resonator has a more stable configuration; i.e., the optical path is entirely composed of an optical fiber to prevent scattering and absorption of a laser beam by air and to reduce the deviation of an optical axis.

In some embodiments, light may be transmitted between the optical resonator and the detector through a space or an optical fiber.

<Arithmetic Device>

The arithmetic device 30 may be of any type that can determine the concentration of a light-absorbing substance in the optical resonator on the basis of the aforementioned decay time and ring-down rate, to calculate the concentration of the carbon isotope from the concentration of the light-absorbing substance.

The arithmetic device 30 includes an arithmetic controller 31, such as an arithmetic unit used in a common computer system (e.g., CPU); an input unit 32, such as a keyboard or a pointing device (e.g., a mouse); a display unit 33, such as an image display (e.g., a liquid crystal display or a monitor); an output unit 34, such as a printer; and a storage 35, such as a ROM, a RAM, or a magnetic disk.

<Isotopic Carbon Dioxide Generator>

The isotopic carbon dioxide generator 40 may be of any type that can convert a carbon isotope into isotopic carbon dioxide. The isotopic carbon dioxide generator 40 preferably has a function of oxidizing a sample to convert carbon contained in the sample into carbon dioxide. The isotopic carbon dioxide generator 40 may be, for example, a carbon dioxide generator (G) 41, such as a total organic carbon (hereinafter may be referred to as "TOC") generator, a sample gas generator for gas chromatography, or a sample gas generator for combustion ion chromatography. Particularly preferred is a TOC generator, which can readily produce isotopic carbon dioxide from a carbon isotope.

A TOC generator produces TOC through removal of inorganic carbon (hereinafter may be referred to as "IC") from total carbon (hereinafter may be referred to as "TC") contained in a sample. Subtraction from IC level from TC level prolongs a total measuring time. In a preferred embodiment, high-purity air is fed to a sample solution for removal of IC, a platinum catalyst is then added to the sample solution, and high-purity air is then fed to the solution under heating, to oxidize TC into carbon dioxide ($CO_2$) for generation of TOC (this process is called "NPOC process"). Although a process involving removal of IC by aeration may lose purgeable organic carbon (POC) (e.g., trihalomethane) during aeration, the process barely affects TOC level because the ratio of purgeable organic carbon to TOC is generally very low.

As used herein, the term "total organic carbon" refers to carbon that binds to a hydrogen, oxygen, and/or nitrogen atom to form an organic compound. As used herein, the term "inorganic carbon" refers to carbon that forms an inorganic substance, such as carbon dioxide, carbonate ion, or hydrogen carbonate ion.

[Experiment for Pretreatment and Introduction of Biological Sample]

The following experiment was performed with a total organic carbon (TOC) analyzer for examining formation of carbon dioxide ($CO_2$) through combustion of a sample and introduction of the sample into an analysis system.

Figure 8:
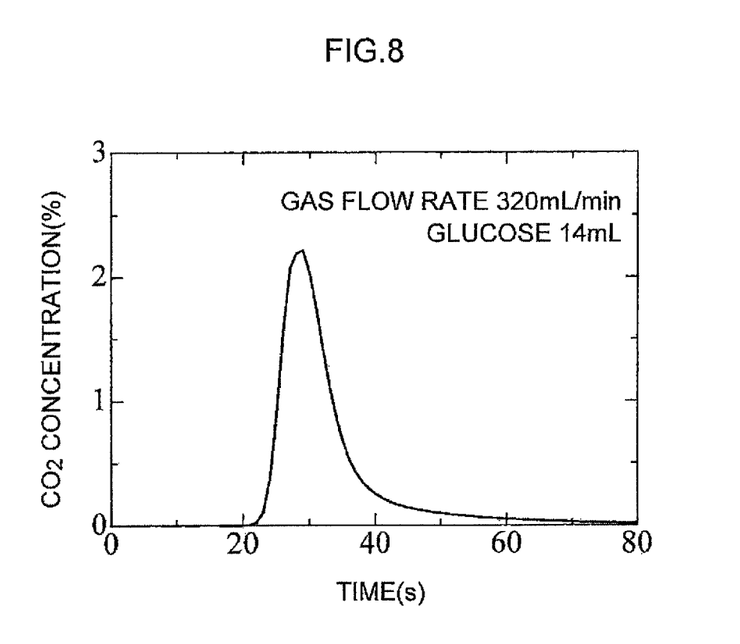
FIG. 8 illustrates a change over time in partial pressure of $CO_2$ in a gas introduced into a CRDS system.

An aqueous glucose solution simulating a biological sample was added dropwise to a ceramic combustion dish, and the dish was placed in the TOC analyzer and then heated at about 900° C. for formation of $CO_2$. The resultant $CO_2$ was introduced into a $CO_2$ concentration meter simulating a CRDS system together with a carrier gas ($O_2$: 99.9% or more+$N_2$: <900 ppm). FIG. 8 illustrates a change in partial pressure of $CO_2$ in the introduced gas mixture over time. In the case of an aqueous glucose solution of 14 μL (carbon content: 70 μgC) and a gas flow rate of 320 mL/min, the time for introduction of $CO_2$ gas was about 20 seconds, and the $CO_2$ partial pressure was 2.2% at a maximum.

The results demonstrated that a biological sample can be converted into carbon dioxide for analysis of a carbon isotope contained in the sample by a CRDS system.

Now will be described comparison of the pretreatment processes of LSC and AMS (which are typical radioactive carbon isotope analyzing techniques prior to the present invention) with the pretreatment process of the present invention involving the use of the principle of TOC with the carbon dioxide generator 41.

The pretreatment process for LSC analysis of a biological sample requires several minutes to about 28 hours, and the pretreatment time varies with the type of a biological sample. The pretreatment processes for analysis of urine and blood will now be described.

In the case of LSC analysis of a urine sample, the sample may optionally be diluted with distilled water. The pretreatment process for the analysis requires several minutes.

In LSC analysis, the intensity of radiation is determined through detection of radiation emitted from a sample and fluorescence emitted from a scintillator. In the case of LSC analysis of a blood sample, a pigment derived from blood may inhibit detection of fluorescence, resulting in failure of correct analysis. In such a case, a pretreatment process may be required which involves addition of, for example, a tissue solubilizer Soluene-350 (manufactured by PerkinElmer) to the blood sample, heating of the mixture at 40° C. to 60° C. for several hours, and addition of 30% hydrogen peroxide to the mixture for decoloration of the pigment. This pretreatment process requires about 4 to 24 hours. An alternative pretreatment process involves drying of the blood sample, oxidation of carbon contained in the sample into carbon dioxide through combustion, and trapping of the resultant carbon dioxide with an amine, for example. This pretreatment process requires about 4 to 24 hours.

The pretreatment process for AMS analysis of a biological sample involves first to fifth steps as schematically described below. Examples of the biological sample include blood, plasma, urine, feces, and bile.

The first step involves optional dilution of a biological sample with a diluent, and fractionation of the diluted sample. The diluent is preferably, for example, ultrapure water or a blank sample.

The second step involves oxidation of the fractionated sample to convert carbon contained in the sample into carbon dioxide.

The third step involves isolation and purification of carbon dioxide from, for example, water or nitrogen. The carbon content of the purified carbon dioxide is determined.

The fourth step involves reduction of the purified carbon dioxide into graphite. For example, the carbon dioxide is reduced into graphite by mixing of the carbon dioxide with iron powder and hydrogen gas (i.e., reductants), and heating of the mixture in an electric furnace.

The fifth step involves pressing of the resultant graphite.

The aforementioned pretreatment process requires about six days.

The pretreatment process for LSC analysis requires several minutes to about 28 hours, and the pretreatment process for AMS analysis requires about six days. In contrast, the pretreatment process according to the present embodiment (i.e., generation of carbon dioxide with the TOC generator) requires several minutes to about 28 hours. Examples of the pretreatment process include dilution, extraction, and concentration. In principle, the pretreatment process is performed until conversion of carbon contained in an analyte into carbon dioxide through complete combustion of the carbon. According to the present embodiment, the pretreatment time is as short as that for LSC analysis.

The performance and dimensions of the carbon isotope analyzer according to the present embodiment are as follows:

Detection sensitivity of the $^{14}C$ analyzer to $^{14}C$: 0.1 dpm/mL
Analytical capacity: 400 samples/day
Dimensions: 2 m×1 m×1 m or less The performance and dimensions of an LSC analyzer are as follows:

Detection sensitivity to $^{14}C$: 10 dpm/mL
Analytical capacity: 400 samples/day
Dimensions: 1 m×1 m×0.5 m The performance and dimensions of an AMS analyzer are as follows:

Detection sensitivity to $^{14}C$: 0.001 dpm/mL
Analytical capacity: 5 samples/day
Dimensions: about 15 m×10 m×3 m Although the carbon isotope analyzer of the present invention has been described with reference to the embodiment, the configuration of the carbon isotope analyzer should not be limited to that described above, and various modifications may be made. Several modifications of the carbon isotope analyzer will now be described by focusing on modified points.

(Modification 1 of Carbon Isotope Analyzer)

Figure 3:
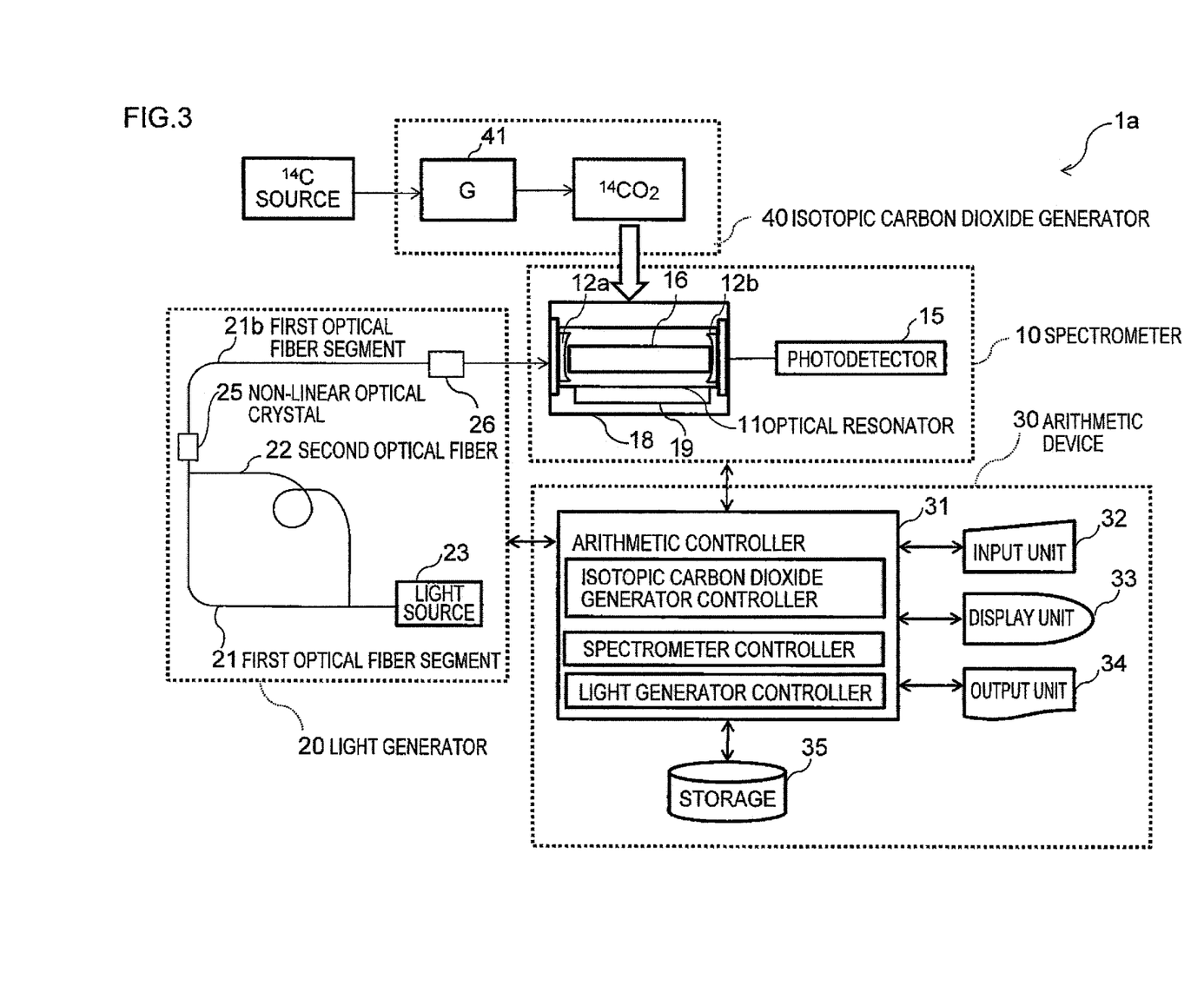
FIG. 3 is a schematic illustration of modification 1 of the carbon isotope analyzer.

FIG. 3 is a schematic illustration of modification 1 of the carbon isotope analyzer. As illustrated in FIG. 3, the spectrometer 10 may further include a Peltier element 19 for cooling the optical resonator 11 and a vacuum unit 18 for accommodating the optical resonator 11. The light absorption of $^{14}CO_2$ has temperature dependence. Thus, a decrease in temperature in the optical resonator 11 with the Peltier element 19 facilitates distinction between $^{14}CO_2$ absorption lines and $^{13}CO_2$ and $^{12}CO_2$ absorption lines and enhances the $^{14}CO_2$ absorption intensity. Disposition of the optical resonator 11 in the vacuum unit 18 prevents the resonator 11 from being exposed to external air, leading to a reduction in effect of the external temperature on the resonator 11 and an improvement in analytical accuracy. The cooler for cooling the optical resonator 11 may be, for example, a liquid nitrogen bath or a dry ice bath besides the Peltier element 19. The Peltier element 19 is preferred in view of a reduction in size of the spectrometer 10, whereas a liquid nitrogen bath or a dry ice bath is preferred in view of a reduction in production cost of the analyzer.

The vacuum unit 18 may be of any type that can accommodate the optical resonator 11, apply light from the light generator 20 to the optical resonator 11, and transmit light to the photodetector.

Figure 4:
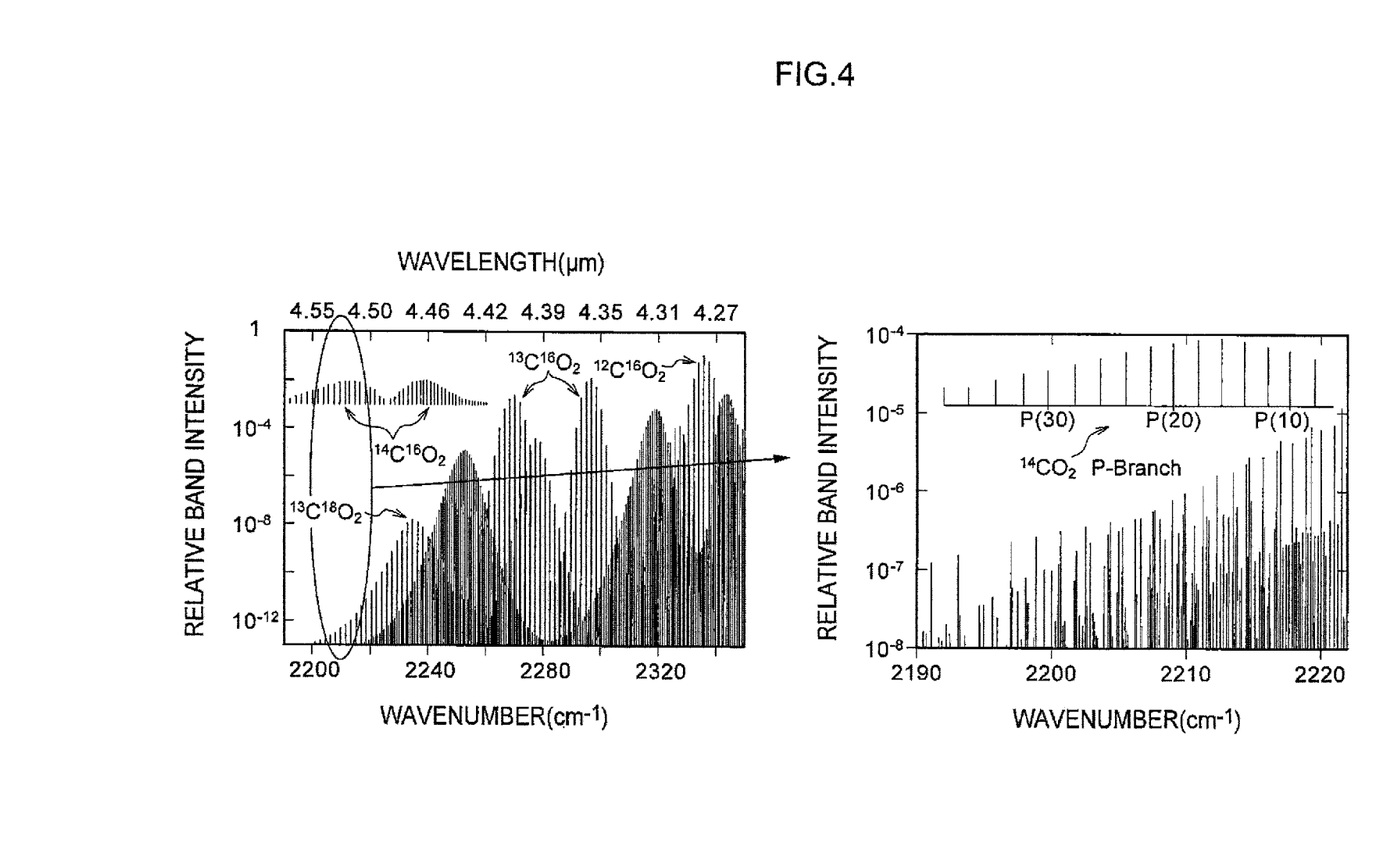
FIG. 4 illustrates the temperature dependence of the absorption lines of $^{14}CO_2$.

FIG. 4 (cited from Applied Physics Vol. 24, pp. 381-386, 1981) illustrates the relationship between the absorption wavelength and absorption intensity of analytes $^{12}C^{16}O_2$, $^{13}C^{18}O_2$, $^{13}C^{16}O_2$, and $^{14}C^{16}O_2$. As illustrated in FIG. 4, each isotopic carbon dioxide has distinct absorption lines. Actual absorption lines have a finite width caused by the pressure and temperature of a sample. Thus, the pressure and temperature of a sample are preferably adjusted to atmospheric pressure or less and 273K (0° C.) or less, respectively.

Since the absorption intensity of $^{14}CO_2$ has temperature dependence as described above, the temperature in the optical resonator 11 is preferably adjusted to a minimum possible level. In detail, the temperature in the optical resonator 11 is preferably adjusted to 273K (0° C.) or less. The lower limit of the temperature may be any level. In view of cooling effect and cost, the temperature in the optical resonator 11 is adjusted to preferably 173K to 253K (−100° C. to −20° C.), particularly preferably about 233K (−40° C.).

The spectrometer may further be provided with a vibration absorber. The vibration absorber can prevent a variation in distance between the mirrors due to the external vibration, resulting in an improvement in analytical accuracy. The vibration absorber may be an impact absorber (polymer gel) or a seismic isolator. The seismic isolator may be of any type that can provide the spectrometer with vibration having a phase opposite to that of the external vibration.

Figure 6:
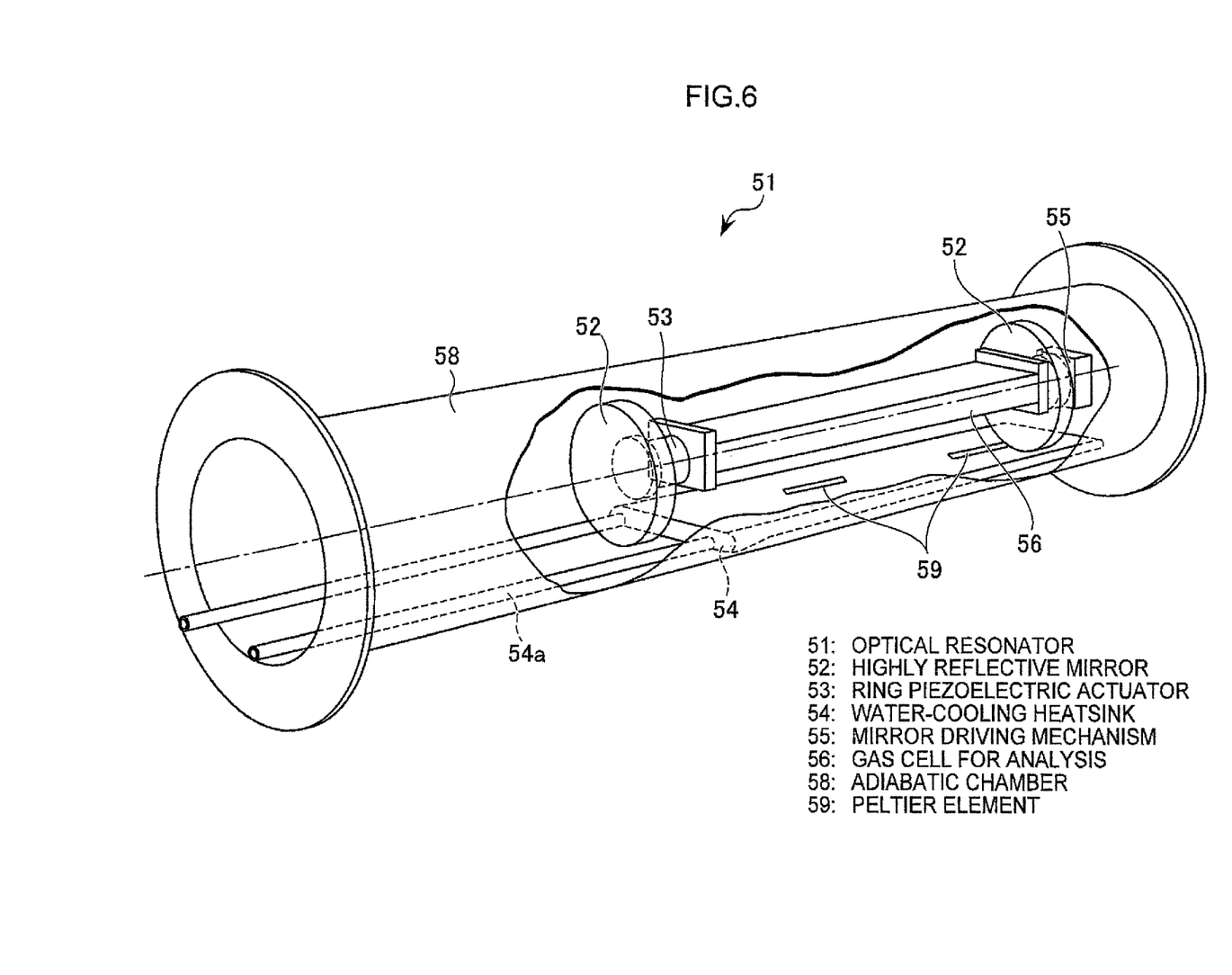
FIG. 6 is a schematic illustration of a modified optical resonator.

FIG. 6 is a schematic illustration (partially cross-sectional view) of a modification of the optical resonator 11. As illustrated in FIG. 6, an optical resonator 51 includes a cylindrical adiabatic chamber (vacuum unit) 58; a gas cell 56 for analysis disposed in the adiabatic chamber 58; a pair of highly reflective mirrors 52 disposed at both ends of the gas cell 56; a mirror driving mechanism 55 disposed at one end of the gas cell 56; a ring piezoelectric actuator 53 disposed on the other end of the gas cell 56; a Peltier element 59 for cooling the gas cell 56; and a water-cooling heatsink 54 provided with a cooling pipe 54a connected to a circulation coiler (not shown).

<Light Shield>

In the aforementioned embodiment, the distance between the mirrors is adjusted with the piezoelectric element 13 for generation of ring-down signals in the spectrometer 10. For generation of ring-down signals, a light shield may be provided in the light generator 20 for ON/OFF control of light incident on the optical resonator 11. The light shield may be of any type that can quickly block light having the absorption wavelength of the isotopic carbon dioxide. The light shield is, for example, an optical switch 26 illustrated in FIG. 3. The incident light should be blocked within a time much shorter than the decay time of light in the optical resonator.

In the aforementioned embodiment, the first optical fiber 21 extends from the light source 23 to the optical resonator 11. The first optical fiber 21 may be composed of a first optical fiber segment 21a extending between the light source 23 and the non-linear optical crystal 25 and a first optical fiber segment 21b for mid-infrared light extending between the non-linear optical crystal 25 and the optical resonator 11. The first optical fiber segment 21b can effectively transmit light of 4.5 µm from the non-linear optical crystal to the optical resonator 11. The first optical fiber segment 21a may be the same type as the first optical fiber 21. The first optical fiber segment 21b may be any mid-infrared optical fiber that barely absorbs light of 4.5 µm region. The first optical fiber segment 21b is preferably a fluoride fiber or a hollow fiber.

The light generator 20 may be provided with a light transmitter for transmitting light from the non-linear optical crystal 25 to the optical resonator 11 instead of the first optical fiber segment 21b illustrated in FIG. 3. The light transmitter may be composed of one or more optical lenses, for example. The light transmitter may be an optical path composed of optical lenses disposed upstream and/or downstream of the non-linear optical crystal, or an optical module including the optical path.

(Modification 2 of Carbon Isotope Analyzer)

FIG. 5 is a schematic illustration of modification 2 of the carbon isotope analyzer. As illustrated in FIG. 5, the spectrometer 10 may further include a diffraction grating 14 for dispersing transmitted light into spectral components of different wavelengths. In this case, the photodetector is preferably composed of a sub-photodetector 15a and a sub-photodetector 15b that detect spectral components of different wavelengths, in view of an improvement in analytical accuracy through analysis of these spectral components of the transmitted light.

The $^{14}$C concentration of a sample gas may be determined on the basis of the intensity of only necessary absorption lines obtained through selection of predetermined light with the optical resonator and selection of wavelengths of transmitted light with the diffraction grating. The diffraction grating disposed in the spectrometer contributes to a further improvement in analytical performance.

(Method of Analyzing Carbon Isotope)

Now will be described a method of analyzing radioisotope $^{14}$C.

(A) The carbon isotope analyzer 1 illustrated in FIG. 1 is provided. A $^{14}$C-containing biological sample (e.g., blood, plasma, urine, feces, or bile) is provided as a radioisotope $^{14}$C source.

(B) A gas containing isotopic carbon dioxide $^{14}CO_2$ (hereinafter referred to as "$^{14}CO_2$ gas") is generated from the radioisotope $^{14}$C source. Preferably, moisture is removed from the resultant $^{14}CO_2$ gas. For example, moisture is preferably removed from the $^{14}CO_2$ gas in the isotopic carbon dioxide generator 40 by allowing the $^{14}CO_2$ gas to pass through a desiccant (e.g., calcium carbonate) or cooling the $^{14}CO_2$ gas for moisture condensation. Formation of ice or frost on the optical resonator 11, which is caused by moisture contained in the $^{14}CO_2$ gas, may lead to a reduction in reflectance of the mirrors, resulting in low detection sensitivity. Thus, removal of moisture improves analytical accuracy. The $^{14}CO_2$ gas is preferably cooled and then introduced into the spectrometer 10 for the subsequent spectroscopic process. Introduction of the $^{14}CO_2$ gas at room temperature significantly varies the temperature of the optical resonator, resulting in a reduction in analytical accuracy.

(C) The $^{14}CO_2$ gas is fed into the optical resonator 11 having the paired mirrors 12a and 12b. The $^{14}CO_2$ gas is preferably cooled to 273K (0° C.) or less in view of an increase in absorption intensity of incident light. The optical resonator 11 is preferably maintained under vacuum because a reduction in effect of the external temperature on the optical resonator improves analytical accuracy.

(D) First light (optical frequency comb) is generated from the light source 23. The first light is transmitted through the first optical fiber 21. The first light is also transmitted through the second optical fiber 22 for wavelength conversion branching from the first optical fiber 21, to generate second light having a wavelength different from that of the first light. The second light is combined with the first light downstream of the first optical fiber 21, and the first light and the second light are transmitted through the non-linear optical crystal 25, to generate incident light of 4.5 µm, which is the absorption wavelength of the isotopic carbon dioxide $^{14}CO_2$.

(E) The incident light is applied to the isotopic carbon dioxide $^{14}CO_2$ and is allowed to resonate. In order to improve analytical accuracy, the external vibration to the optical resonator 11 is preferably absorbed by a vibration absorber to prevent a variation in distance between the mirrors 12a and 12b. During application of the incident light, the downstream end of the first optical fiber 21 is preferably brought into contact with the mirror 12a to prevent the incident light from coming into contact with air. The intensity of light transmitted from the optical resonator 11 is then determined. As illustrated in FIG. 5, the transmitted light may be dispersed into spectral components, and the intensities of the spectral components may be determined.

(F) The concentration of carbon isotope $^{14}$C is calculated on the basis of the intensity of the transmitted light.

Other Embodiments

Although the embodiment of the present invention has been described above, the descriptions and drawings as part of this disclosure should not be construed to limit the present invention. This disclosure will enable those skilled in the art to find various alternative embodiments, examples, and operational techniques.

The carbon isotope analyzer according to the embodiment has been described by focusing on the case where the analyte is radioisotope $^{14}$C. The carbon isotope analyzer can analyze stable isotopes $^{12}$C and $^{13}$C besides radioisotope $^{14}$C. In such a case, incident light of 2 µm or 1.6 µm is preferably used for, for example, absorption line analysis of $^{12}CO_2$ or $^{13}CO_2$ on the basis of analysis of $^{12}$C or $^{13}$C.

In the case of absorption line analysis of $^{12}CO_2$ or $^{13}CO_2$, the distance between the mirrors is preferably 10 to 60 cm, and the curvature radius of the mirrors is preferably equal to or longer than the distance therebetween.

Although the carbon isotopes $^{12}$C, $^{13}$C, and $^{14}$C exhibit the same chemical behavior, the natural abundance of $^{14}$C (radioisotope) is lower than that of $^{12}$C or $^{13}$C (stable isotope). Artificial enrichment of the radioisotope $^{14}$C and accurate analysis of the isotope can be applied to observation of a variety of reactions.

The carbon isotope analyzer according to the embodiment may further be provided with a third optical fiber composed of a non-linear fiber that branches from the first optical fiber and combines with the first optical fiber downstream of the branching point. Combination of the first to third optical fibers can generate light of two or more different frequencies.

A medical diagnostic device or environmental measuring device including the configuration described above in the embodiment can be produced as in the carbon isotope analyzer.

As described above, the present invention certainly includes, for example, various embodiments not described herein. Thus, the technological range of the present invention is defined by only claimed elements of the present invention in accordance with the proper claims through the above descriptions.

REFERENCE SIGNS LIST

1: Carbon isotope analyzer
10: Spectrometer
11: Optical resonator
12: Mirror
13: Piezoelectric element
14: Diffraction grating
15: Photodetector
16: Cell
18: Vacuum unit
19: Peltier element
20: Light generator
21: First optical fiber
22: Second optical fiber
23: Light source
25: Non-linear optical crystal
26: Optical switch
30: Arithmetic device
40: Isotopic carbon dioxide generator

The invention claimed is:

1. A carbon isotope analyzer comprising:
an isotopic carbon dioxide generator to generate isotopic carbon dioxide from a carbon isotope;
a spectrometer comprising an optical resonator having a pair of mirrors, and a photodetector to determine the intensity of light transmitted from the optical resonator; and
a light generator,
wherein the intensity of the transmitted light is determined while the isotopic carbon dioxide is cooled, via a cooling device, to 273K(0° C.) or less.

2. The carbon isotope analyzer according to claim 1, wherein the carbon isotope is radioactive carbon $^{14}C$, and the isotopic carbon dioxide is radioactive carbon dioxide $^{14}CO_2$.

3. The carbon isotope analyzer according to claim 1, wherein the light generator includes a light source that generates an optical frequency comb.

4. The carbon isotope analyzer according to claim 1, wherein the light generator includes a fiber laser source.

5. The carbon isotope analyzer according to claim 1, wherein the light generator includes a non-linear optical crystal to generate light having an absorption wavelength of the isotopic carbon dioxide of 4.5 μm region.

6. The carbon isotope analyzer according to claim 1, wherein the isotopic carbon dioxide generator generates the isotopic carbon dioxide from the carbon isotope with a total organic carbon generator.

7. The carbon isotope analyzer according to claim 1, wherein the light generator further comprises a light transmitter to transmit light from a non-linear optical crystal to the optical resonator.

8. The carbon isotope analyzer according to claim 1, wherein the spectrometer further comprises a cooler to cool the optical resonator.

9. The carbon isotope analyzer according to claim 1, wherein the spectrometer further comprises a vacuum unit accommodating the optical resonator.

10. The carbon isotope analyzer according to claim 1, wherein the spectrometer further comprises a vibration absorber.

11. The carbon isotope analyzer according to claim 1, wherein the spectrometer further comprises a diffraction grating to disperse the transmitted light into spectral components of different wavelengths, and the photodetector comprises a sub-photodetector a and a sub-photodetector b to detect the spectral components of different wavelengths.

12. A method of analyzing a carbon isotope, comprising:
forming isotopic carbon dioxide from a carbon isotope;
feeding the isotopic carbon dioxide into an optical resonator having a pair of mirrors;
generating a plurality of light beams having different wavelengths from a light source, and transmitting the light beams through an optical crystal, to generate incident light;
applying the incident light to the isotopic carbon dioxide, and determining the intensity of transmitted light generated through resonance of the incident light; and
calculating the concentration of the carbon isotope on the basis of the intensity of the transmitted light,
wherein the intensity of the transmitted light is determined while the isotopic carbon dioxide is cooled, via a cooling device, to 273K(0° C.) or less.

13. The method according to claim 12, wherein the carbon isotope is radioactive carbon $^{14}C$, and the isotopic carbon dioxide is radioactive carbon dioxide $^{14}CO_2$.

14. The method according to claim 12, wherein the incident light is light of 4.5 μm region.

15. The method according to claim 12, wherein an optical frequency comb is generated from the light source.

* * * * *